US011432948B2

(12) United States Patent
Slater (10) Patent No.: US 11,432,948 B2
(45) Date of Patent: Sep. 6, 2022

(54) PROSTHETIC SOCK MANAGEMENT TOOL

(71) Applicant: United States Department of Veterans Affairs, Washington, DC (US)

(72) Inventor: Billie Caris Savvas Slater, Mendota Heights, MN (US)

(73) Assignee: United States Government as represented by the Department of Veterans Affair, Washington, DC (US)

(*) Notice: Subject to any disclaimer, the term of this patent is extended or adjusted under 35 U.S.C. 154(b) by 662 days.

(21) Appl. No.: 16/451,527

(22) Filed: Jun. 25, 2019

(65) Prior Publication Data
US 2019/0388249 A1    Dec. 26, 2019

Related U.S. Application Data

(60) Provisional application No. 62/689,575, filed on Jun. 25, 2018.

(51) Int. Cl.
*A61F 2/76* (2006.01)
*A61B 5/00* (2006.01)
*A61F 2/78* (2006.01)
*A61F 2/80* (2006.01)

(52) U.S. Cl.
CPC .............. *A61F 2/76* (2013.01); *A61B 5/4851* (2013.01); *A61F 2/7812* (2013.01); *A61F 2/80* (2013.01); *A61F 2002/7615* (2013.01); *A61F 2002/7818* (2013.01)

(58) Field of Classification Search
CPC .. A61F 2/76; A61F 2/7812; A61F 2/80; A61F 2002/7615; A61F 2002/7818; A61F 2002/7812; D06F 95/002; D06F 95/004
See application file for complete search history.

(56) References Cited

U.S. PATENT DOCUMENTS

| D294,757 | S  | * | 3/1988  | Kahane ........................ D3/273 |
| 4,880,315 | A  | * | 11/1989 | Berry ..................... A45C 13/02 150/113 |
| 7,775,365 | B1 | * | 8/2010  | More ........................ A61F 2/76 206/572 |
| 8,181,775 | B2 | * | 5/2012  | Bunn ..................... A45C 13/03 206/466 |
| 10,927,494 | B1 | * | 2/2021 | Sayarat .................. A47G 25/14 |
| 2003/0179959 | A1 | * | 9/2003 | Nishi ................... D06F 95/006 383/117 |
| 2005/0232519 | A1 | * | 10/2005 | Grimes, Jr. .......... D06F 95/006 383/117 |
| 2006/0213963 | A1 | * | 9/2006 | Session, Sr. ......... D06F 95/006 232/1 B |
| 2017/0215616 | A1 | * | 8/2017 | Cunningham ........ D06F 95/008 |
| 2018/0038043 | A1 | * | 2/2018 | Johnson ............... D06F 95/004 |

* cited by examiner

*Primary Examiner* — Bruce E Snow
(74) *Attorney, Agent, or Firm* — Ballard Spahr LLP (57) ABSTRACT

A device and method for managing a plurality of groups of socks where the device includes a plurality of pouches attached to one another and a patient education and compliance tool. Each group has at least one sock. Socks of each of the groups have different characteristics from one another. The groups of socks are adapted for use between a limb of a patent and a socket of a prosthetic device. Each pouch is adapted for securing at least one sock from a group. The method includes sorting the plurality of groups of socks according to the characteristic, associating each pouch with a respective one of the groups, and securing each group of socks within an associated pouch.

18 Claims, 8 Drawing Sheets

PROSTHETIC SOCK MANAGEMENT TOOL

CROSS REFERENCE TO RELATED APPLICATION

This application is based upon and claims priority to U.S. Provisional Application No. 62/689,575, filed Jun. 25, 2018, which provisional application is hereby incorporated by reference herein.

STATEMENT REGARDING FEDERALLY SPONSORED RESEARCH

This invention was made with government support from the VHA Innovators Network Program awarded by the Department of Veterans Affairs. The government has certain rights in the invention.

FIELD OF THE INVENTION

This disclosure relates to a prosthetic sock management tool, and more particularly to a prosthetic sock management tool having a plurality of washable pouches and patient education materials that are connectable to the plurality of washable pouches. The plurality of pouches may also be color-coded, have numeric identifiers, and/or other indicia that identify and distinguish each pouch from the others. The prosthetic sock management tool also includes a patient education and compliance component, which provides instructions and guidance to patients about how to utilize the prosthetic socks for optimal fit and how to care and maintain the prosthetic socks for optimal performance.

BACKGROUND

The proper use and care of prosthetic socks can be challenging for people with lower limb amputations who use prosthetic sockets for prostheses. Patients who have had a lower limb amputation and use a prosthesis for transfers and/or mobility, must carefully manage the condition of their residual limb to avoid skin breakdown, callous formation, and any other damage to the integrity of the stump. There may be volume changes in the residual limb throughout the course of the day. Many patients manage this fluctuation by donning and doffing socks of various ply. Because the sock changes are made throughout the day, patients must have a variety of socks with them wherever they are, whether it be at home or away. Because it is inconvenient to carry a variety of socks with them, some patients may be noncompliant and do not change their socks as frequently as would be necessary to optimize both fit and comfort. The result of this can be skin breakdown and decrease in levels of comfort. These are both serious issues, as skin breakdown can make it necessary that the person not use the prosthetic limb while the skin wound heals. Uncomfortable fit of the prosthesis may result in less time wearing the prosthesis.

Additionally, these socks must be washed and dried daily to provide a cleaner environment between the limb liner and the socket. Patient noncompliance with this requirement can lead to skin problems. Also repeated use of the same sock without laundering or alternating between socks will lead to crushing and stiffening of the fabric fibers so that they no longer provide an adequate cushion to the limb as it contacts with the socket. Patients may also experience a loss of socks in the washing machine, as people may experience with usual socks.

Thus, there is a need for devices, systems and methods that address one or more of the deficiencies in the current patient prosthetics care as described herein.

SUMMARY

Disclosed herein, in various aspects, is a prosthetic sock management tool including patient education materials. The prosthetic sock management tool consists of two components; a plurality of washable pouches; and patient education and compliance tool connectable to the first component. The plurality of washable pouches may include colored zippers, numeric identifiers, zipper pulls, or other indicia to identify and distinguish each pouch from the others. The assembly may also be made from a quick-dry material. The patient education and compliance tool may include a detachable laminated card that is printed with easy-to-read instructions for the proper use of and care for prosthetic socks.

In an example embodiment of a device for managing a plurality of groups of socks, each group comprises at least one sock, socks of each of the groups have different characteristics. As an example, the device comprises a plurality of pouches attached to one another. Each pouch is adapter for containing at least one sock from one of the groups. In an example one pouch is adapted for securing accessories.

As an example the device further comprises at least one patent education and compliance tool attached to the plurality of pouches. In an example, each of the plurality of pouches is attached to a substrate.

In an example each pouch defines an opening for receiving the socks. In a particular example, at least one of the pouches further comprises a fastening device for closing the opening. In a particular example, the fastening device is selected from a group consisting of: zippers, hook and loop fasteners, snap closures, buttons and magnetic closures.

As an example each pouch is constructed of a washable material. In an example each pouch is constructed of a quick-drying material. In an example, at least one pouch comprises a mesh material. As an example, each pouch is constructed of a different colored material. In a particular example, each pouch is color coded, each pouch corresponding to a respective one of the group of socks.

In an example, each pouch comprises an identifier corresponding to one of the group. In a particular example the identifiers comprise indicia selected from the group consisting of numbers, letters, Braille, and combinations thereof. In a particular example, the fastening device is a zipper. The zipper comprises a zipper pull attached to the zipper. The zipper pull comprises an identifier corresponding to one group.

As an example, the patient education and compliance tool comprises instructions for use and care of the plurality of groups of socks. In an example, the device further comprises a fastener for removably attaching the patent education and compliance tool, thereto. The faster is selected from the group consisting of D-rings, hook and loop fasteners, and magnets.

The invention further comprise a method for managing a plurality of groups of socks. Each group comprises at least one sock. Socks of each of the groups having different characteristics from one another. The method comprises:

sorting the plurality of groups of socks according to the characteristics of the socks;

associating each pouch with a respective one of said groups; and securing each group of socks within an associated one of the pouches respectively.

In an example, sorting the plurality of groups of socks comprises sorting the socks according to a thickness of said socks. As an example the associating step comprises associating each of the pouches with a respective color.

In an example, the associating step comprises associating a unique identifier with each said pouch. In a particular example the unique identifier is selected from the group consisting of numbers, letters, Braille, and combinations thereof.

In an example, sorting the plurality of groups of socks comprises associating a unique identifier with the socks within each group of socks respectively.

These and other features and advantages of the present invention will become more readily apparent when taken into consideration with the following description, the attached drawings, and the claims.

DETAILED DESCRIPTION

The present disclosure can be understood more readily by reference to the following detailed description of the invention, the figures and the examples included herein.

The present invention now will be described more fully hereinafter with reference to the accompanying drawings, in which some, but not all embodiments of the invention are shown. Indeed, this invention may be embodied in many different forms and should not be construed as limited to the embodiments set forth herein; rather, these embodiments are provided so that this disclosure will satisfy applicable legal requirements. Like numbers refer to like elements throughout. It is to be understood that this invention is not limited to the particular methodology and protocols described, as such may vary. It is also to be understood that the terminology used herein is for the purpose of describing particular embodiments only, and is not intended to limit the scope of the present invention.

Many modifications and other embodiments of the invention set forth herein will come to mind to one skilled in the art to which the invention pertains having the benefit of the teachings presented in the foregoing description and the associated drawings. Therefore, it is to be understood that the invention is not to be limited to the specific embodiments disclosed and that modifications and other embodiments are intended to be included within the scope of the appended claims. Although specific terms are employed herein, they are used in a generic and descriptive sense only and not for purposes of limitation.

Moreover, it is to be understood that unless otherwise expressly stated, it is in no way intended that any method set forth herein be construed as requiring that its steps be performed in a specific order. Accordingly, where a method claim does not actually recite an order to be followed by its steps or it is not otherwise specifically stated in the claims or descriptions that the steps are to be limited to a specific order, it is in no way intended that an order be inferred, in any respect. This holds for any possible non-express basis for interpretation, including matters of logic with respect to arrangement of steps or operational flow, plain meaning derived from grammatical organization or punctuation, and the number or type of aspects described in the specification.

All publications mentioned herein are incorporated herein by reference to disclose and describe the methods and/or materials in connection with which the publications are cited. The publications discussed herein are provided solely for their disclosure prior to the filing date of the present application. Nothing herein is to be construed as an admission that the present invention is not entitled to antedate such publication by virtue of prior invention. Further, the dates of publication provided herein can be different from the actual publication dates, which can require independent confirmation.

Definitions

As used in the specification and the appended claims, the singular forms "a," "an" and "the" include plural referents unless the context clearly dictates otherwise.

The word "or" as used herein means any one member of a particular list and also includes any combination of members of that list.

Throughout the description and claims of this specification, the word "comprise" and variations of the word, such as "comprising" and "comprises," means "including but not limited to," and is not intended to exclude, for example, other additives, components, integers or steps. In particular, in methods stated as comprising one or more steps or operations it is specifically contemplated that each step comprises what is listed (unless that step includes a limiting term such as "consisting of"), meaning that each step is not intended to exclude, for example, other additives, components, integers or steps that are not listed in the step.

Ranges can be expressed herein as from "about" or "approximately" one particular value, and/or to "about" or "approximately" another particular value. When such a range is expressed, a further aspect includes from the one particular value and/or to the other particular value. Similarly, when values are expressed as approximations, by use of the antecedent "about," or "approximately," it will be understood that the particular value forms a further aspect. It will be further understood that the endpoints of each of the ranges are significant both in relation to the other endpoint and independently of the other endpoint. It is also understood that there are a number of values disclosed herein and that each value is also herein disclosed as "about" that particular value in addition to the value itself. For example, if the value "10" is disclosed, then "about 10" is also disclosed. It is also understood that each unit between two particular units is also disclosed. For example, if 10 and 15 are disclosed, then 11, 12, 13, and 14 are also disclosed. Similarly, in some optional aspects, when values are approximated by use of the term "substantially," it is contemplated that values within up to 15%, up to 10%, or up to 5% (above or below) of the particular value can be included within the scope of those aspects.

As used herein, the terms "optional" or "optionally" mean that the subsequently described event or circumstance may or may not occur and that the description includes instances where said event or circumstance occurs and instances where it does not.

Disclosed herein, in various aspects, is an innovative approach to address an unmet need for patients, for example, veterans, who are using lower limb prosthetics.

Figure 1:
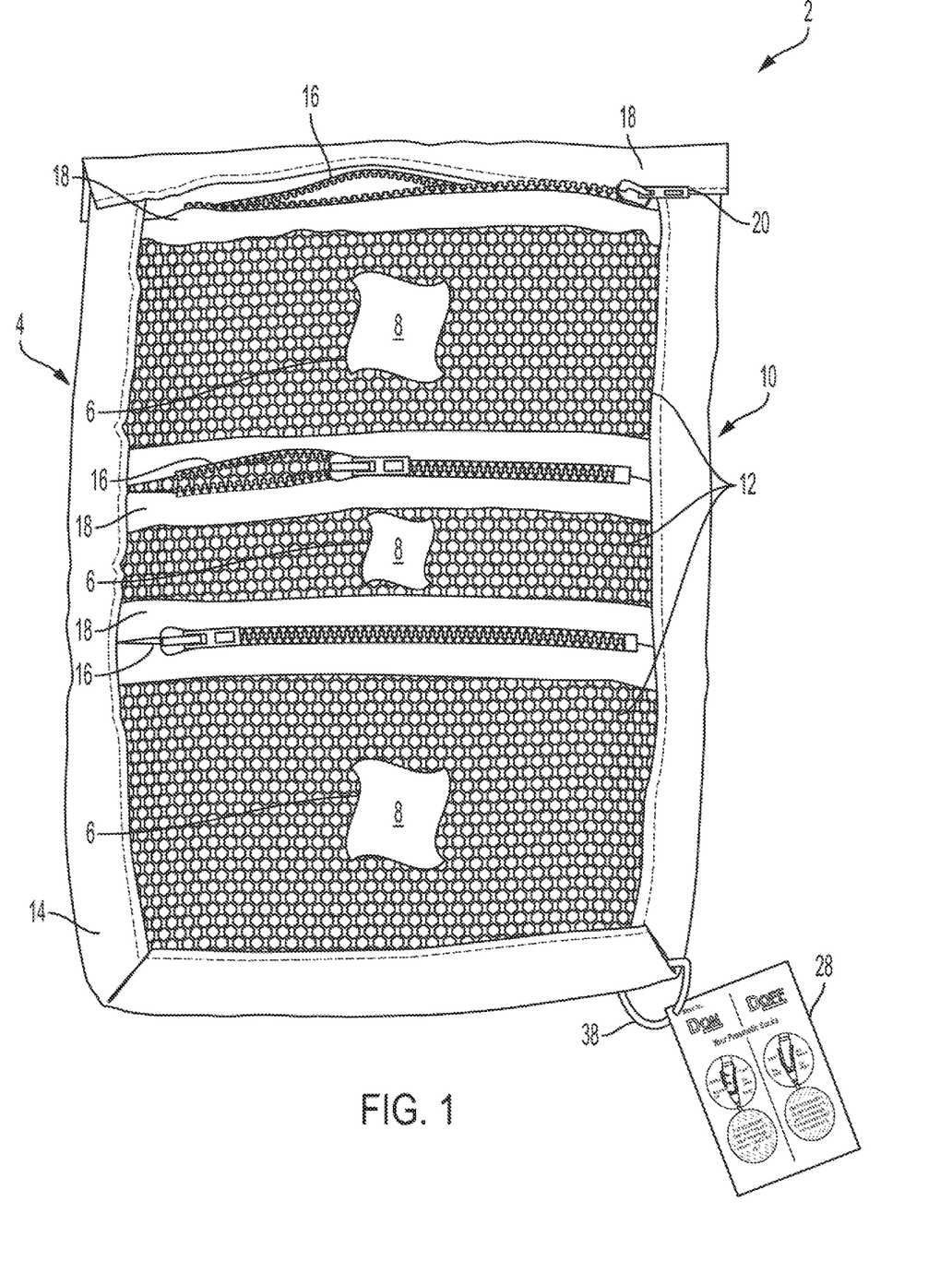
FIG. 1 is a partially cut-away elevation view of an example embodiment of a device for managing a plurality of groups of socks, illustrating socks within pouches.

This invention concerns a device 2 for managing a plurality 4 of groups 6 of socks 8, as shown in FIG. 1. Each group 6 comprises at least one sock 8. Socks 8 of each of the groups 6 have different characteristics from one another. The plurality 4 of groups 6 of socks 8 are adapted for use between a limb of a patient and a socket of a prosthesis. The device 2 comprises a plurality 10 of pouches 12 attached to one another. Each pouch 12 is adapted for securing at least one sock 8 from one of the groups 6.

As shown in FIG. 1, each pouch 12 of the plurality of pouches 10 is attached to a substrate 14. In addition, each pouch 12 defines a respective opening 16 for receiving the socks 8. Each pouch 12 may comprise a fastening device 18 for closing the opening 16, thereby containing each group 6 of socks 8 within each of the plurality 10 of pouches 12. The plurality 10 of pouches 12 with the respective openings 16 are closed via the fastening device 18. As an example, shown in FIG. 2, the fastening devices 18 may be zippers 20. Other examples of fastening devices 18, shown in FIGS. 2A, 2B and 2C include hook and loop fasteners 21 (Velcro™) (FIG. 2A), snap closures 23 (FIG. 2B), buttons 25 (FIG. 2C), magnetic closures 29 (FIG. 2D), or any other fasteners known in the art. The fastening device 18 may include a specially designed zipper pull or handle to allow users with limited dexterity to easily open and close the pouches.

Figure 2:
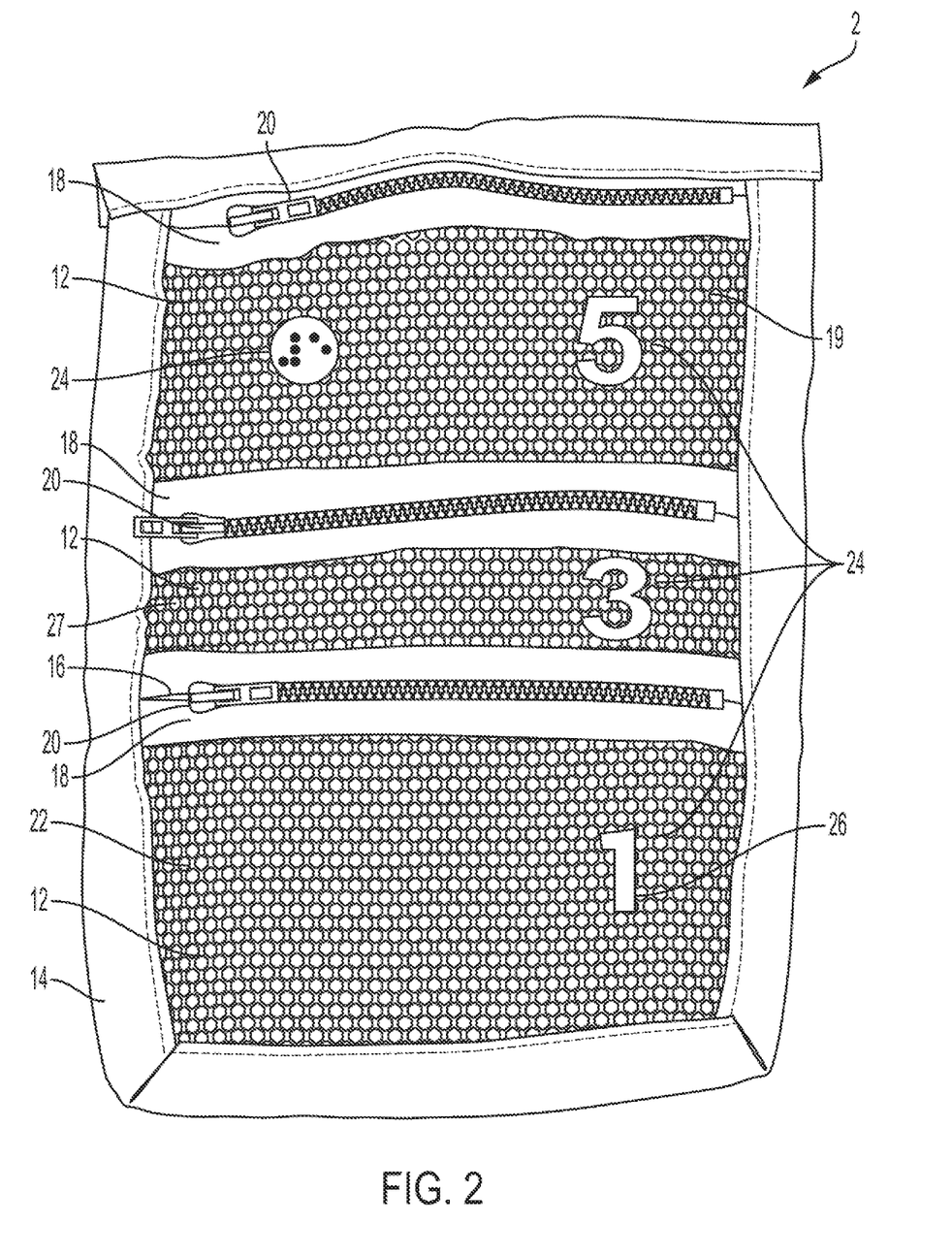
FIG. 2 is an elevation view of an example embodiment of a device for managing a plurality of groups of socks illustrating identifiers on each pouch.
Figure 2A:
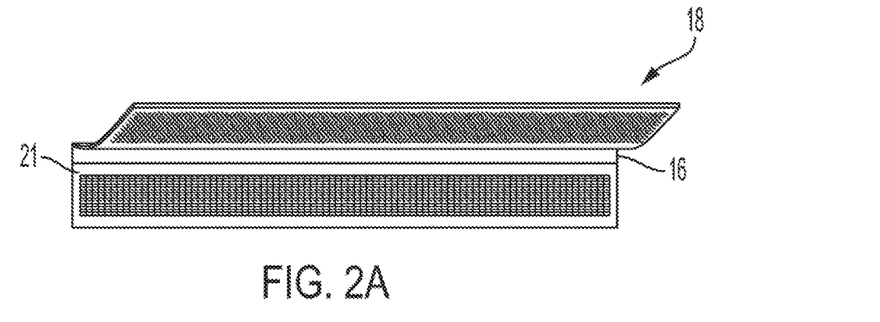
FIGS. 2A, 2B, 2C and 2D are partial views of an example embodiment illustrating various fastening devices.
Figure 2B:
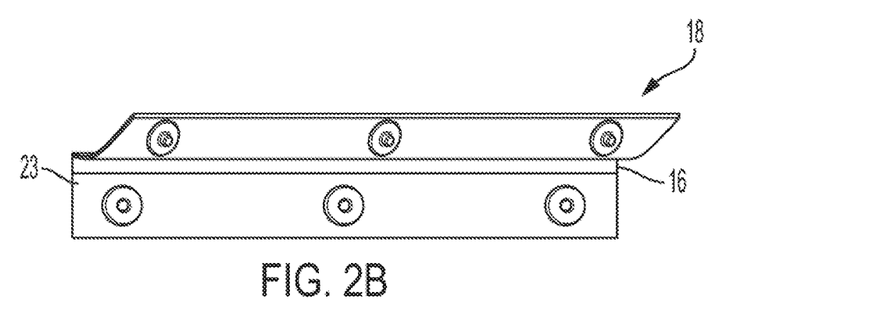
Figure 2C:
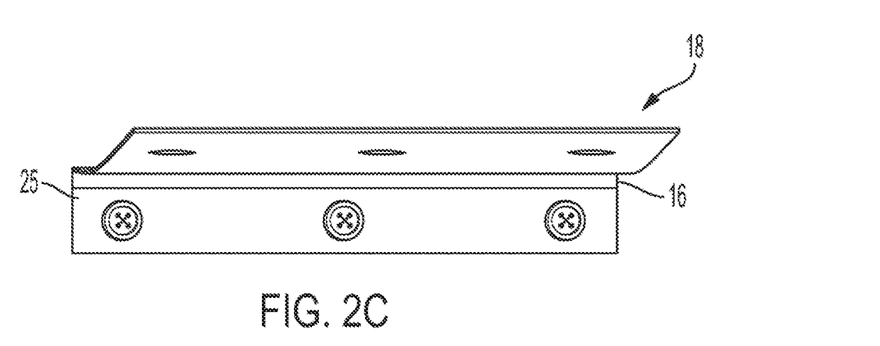
Figure 2D:
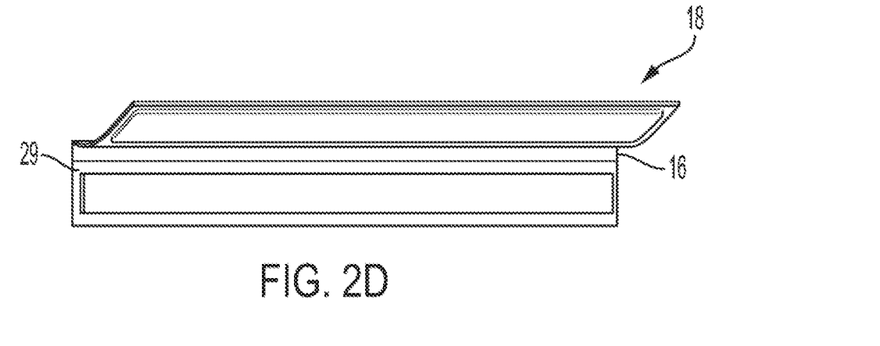
Figure 3:
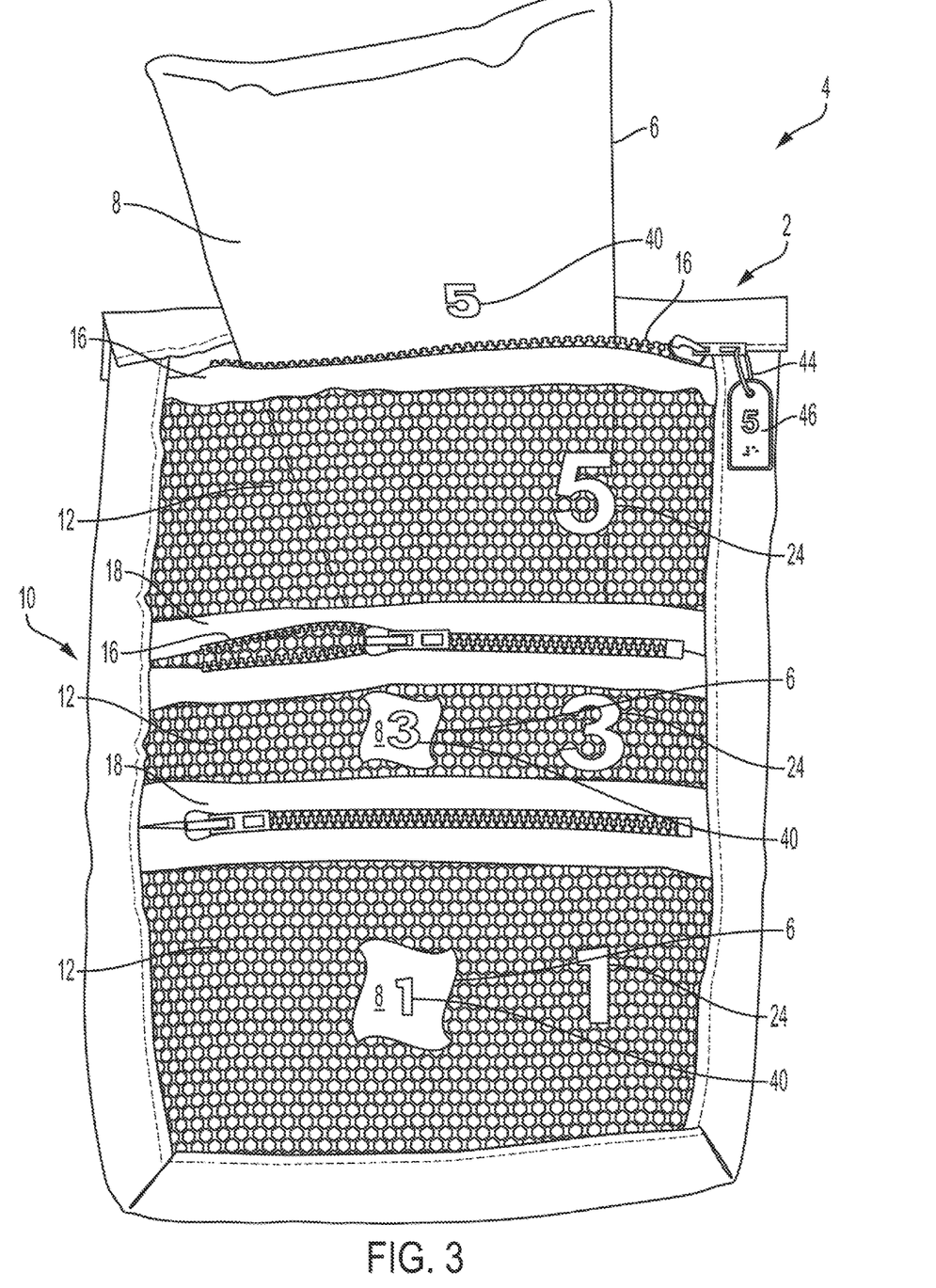
FIG. 3 is a partially cut-away elevation view of an example embodiment of a device for managing a plurality of groups of socks illustrating an open pouch, a sock inserted within the pouch, and an identifier on the sock.

As shown in FIG. 2, at least one pouch 12 may comprises a mesh material 19. Each pouch 12 may be constructed of a washable material 22, or constructed of a quick drying material 27. As shown in FIG. 3, socks 8 can be inserted into pouches 12. The plurality 10 of pouches 12 may be placed into a washing machine, facilitating the laundering process and thereby reducing the risk of losing or misplacing the socks 8.

As shown in FIG. 1, within a plurality 10, each of pouches 12 may be constructed of a different colored material. As an example, each pouch 12 may be color coded to correspond to a respective group 6. As shown in FIG. 3, each pouch 12 may comprise identifier 24 coded to correspond to one of group 6. A zipper pull 44, attached to the fastening device 18 may also comprise a zipper pull identifier 46. An example, shown in FIG. 2, the identifiers 24 may comprise raised numbers. The identifiers may further comprise raised letters, or Braille (FIG. 2).

Figure 4:
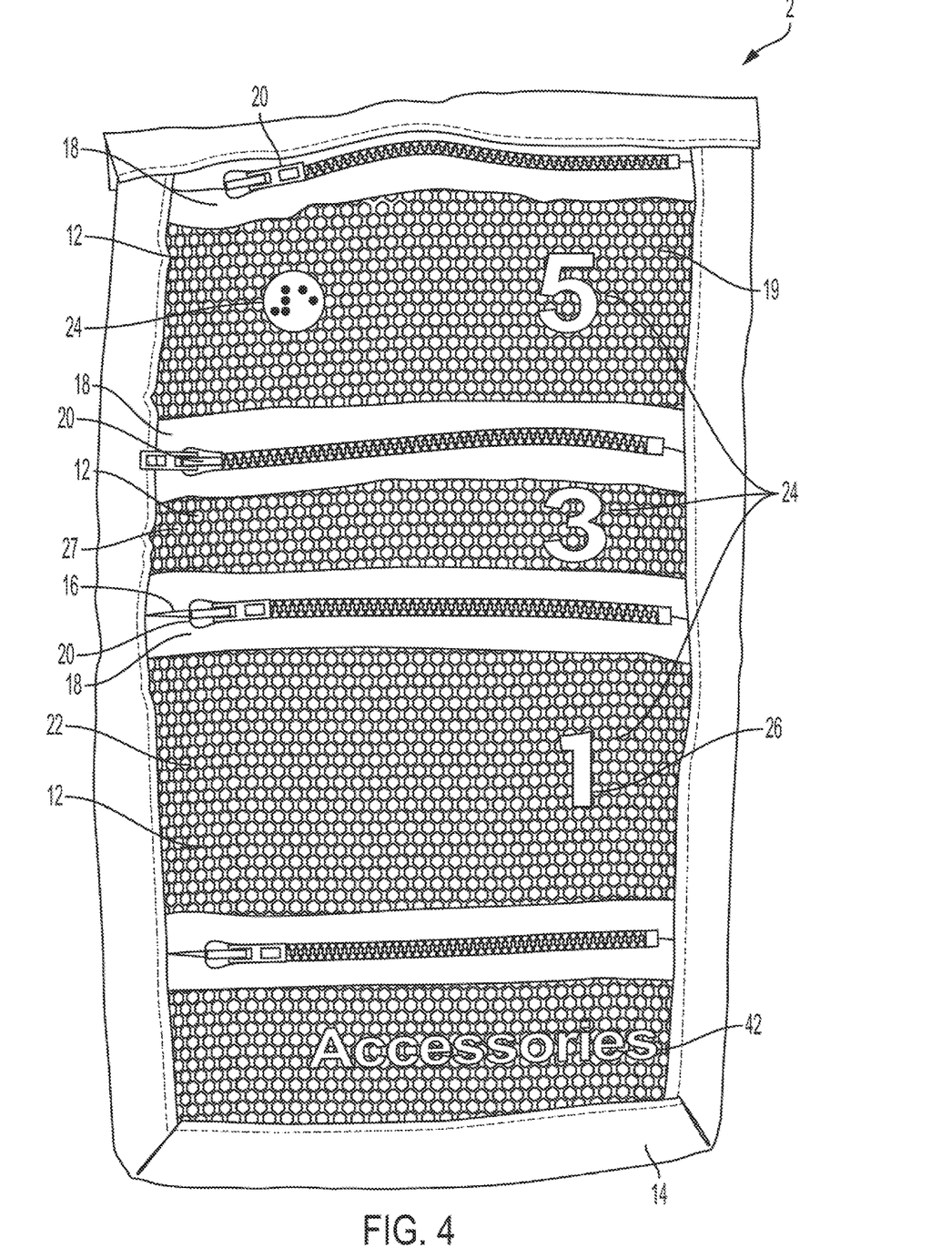
FIG. 4 is an elevation view of an example embodiment of a device for managing a plurality of groups of socks illustrating one pouch for securing accessories.

FIG. 4 illustrates another embodiment of the device where one of the pouches may be adapted to secure accessories 42. The patient may include accessories such as a spray bottle, baby powder, a drying cloth or instructions in the pouch adapted for accessories 42.

Figure 5A:
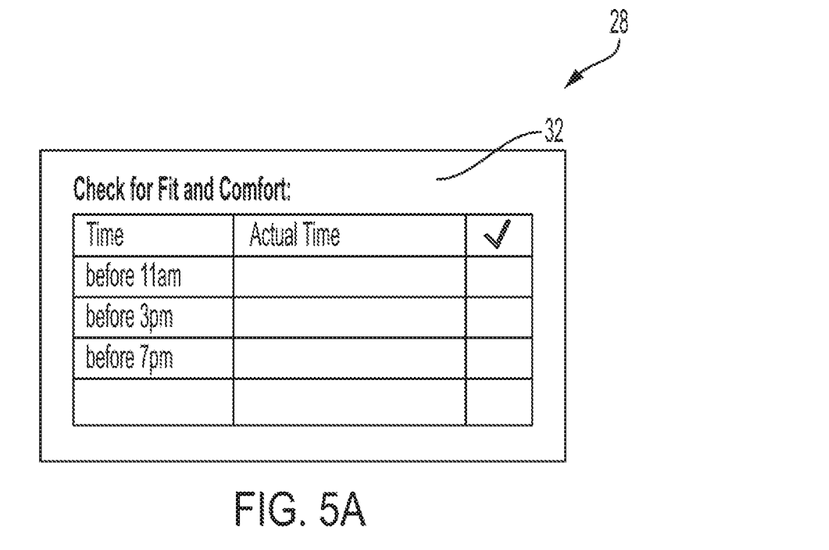
FIGS. 5A, 5B and 5C are illustrations of an example embodiment of the patent education and compliance tool.
Figure 5B:
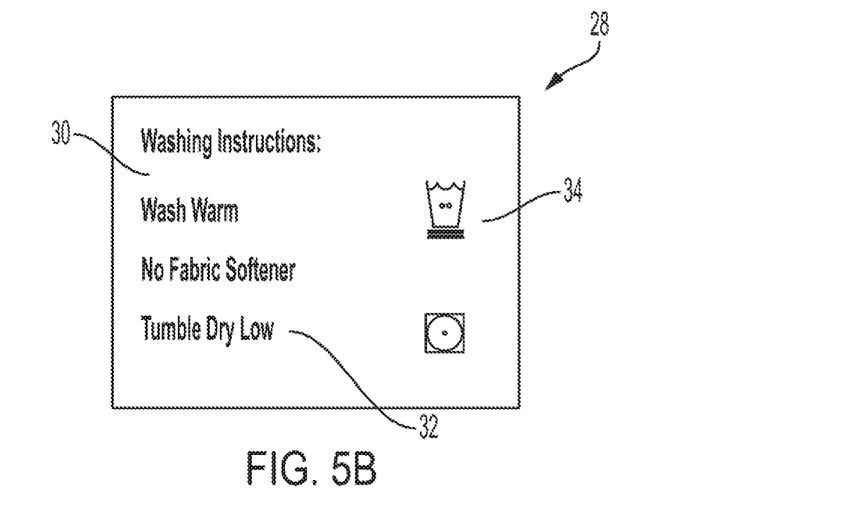
Figure 5C:
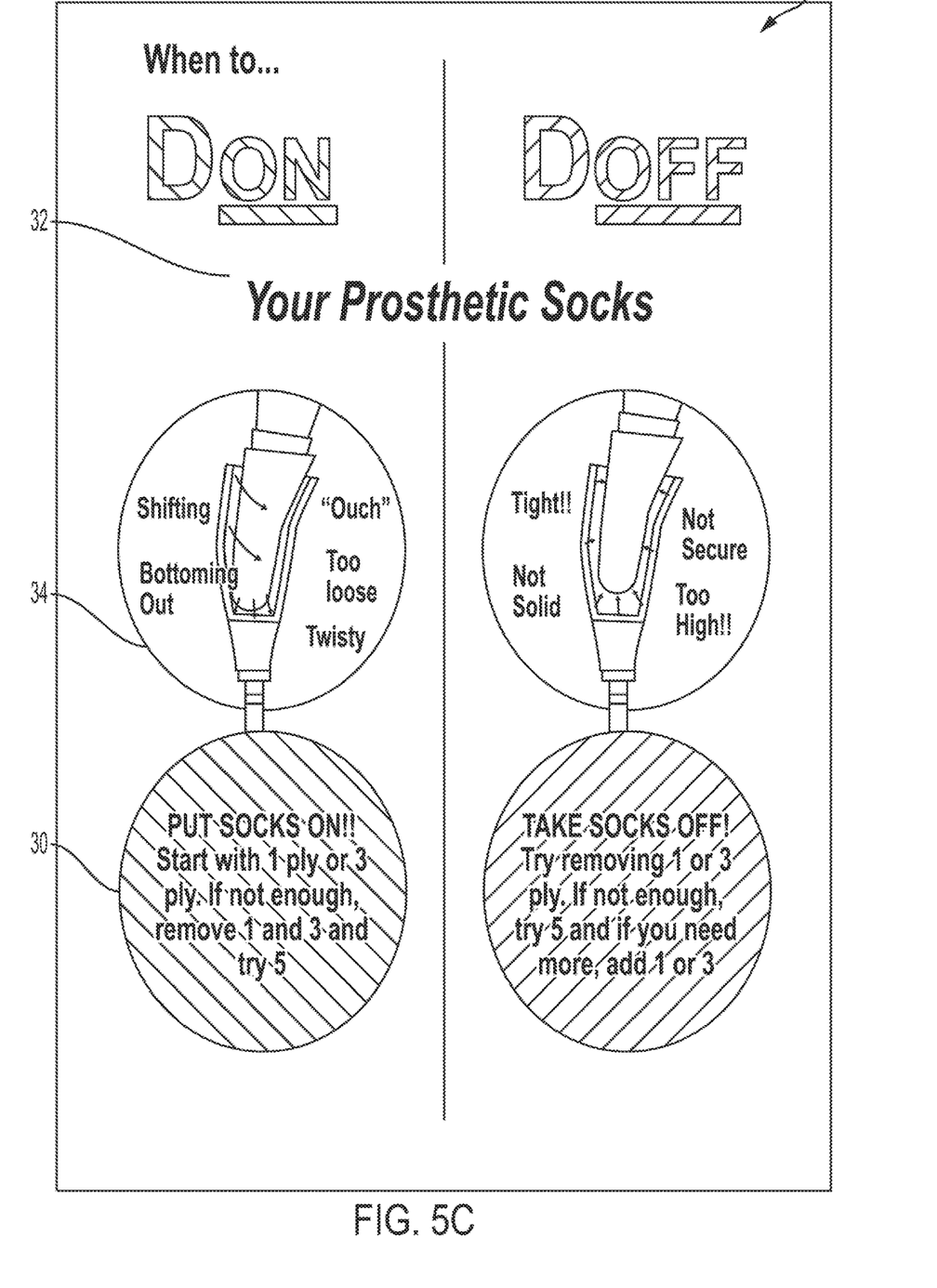

As illustrated in FIG. 1, the device 2 also comprises at least one patient education and compliance tool 28. As illustrated in the examples shown in FIGS. 5A, 5B, and 5C, the education and compliance tool 28 may comprise instructions for use and care 30 of the plurality 4 of groups 6 of socks 8 (FIG. 1). The instructions may comprises writing 32 and illustrated images 34. As an example, FIGS. 5A-5C show the instructions in writing 32 and FIGS. 5B and 5C show illustrated images 34. The instructions may also comprises raised print, Braille or both. As shown in FIG. 1, the patent education and compliance tool 28 may be removably attached to the plurality 10 of pouches 12. As an example, the tool 28 is removable attached via D-ring 38. Other examples of the removable attachment comprise hook and loop fasteners (Velcro™), magnets, and other attachments known in the art. The patient education and compliance tool 28 may also be printed directly on the substrate 14.

Figure 6:
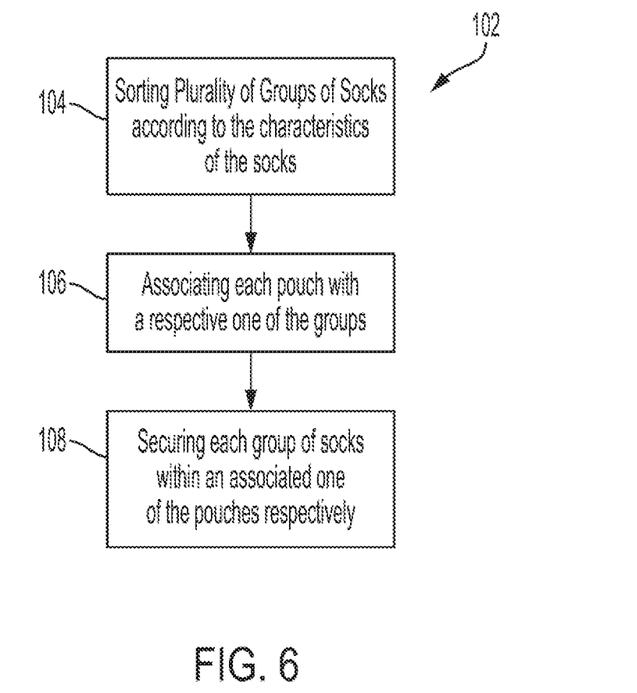
FIG. 6 is a flow chart of an example embodiment of a method for managing a plurality of groups of socks.

A flow chart of an example method 102 for managing a plurality 4 of groups 6 of socks 8 is included in FIG. 6. The method comprises: sorting the plurality of groups of socks according to the characteristics of the socks (step 104); associating each pouch with a respective one of the groups (step 106); and securing each group of socks within an associated one of the pouches respectively (step 108).

Sorting the plurality of groups of socks (step 104) may comprise sorting according to thickness. As an example, shown in FIG. 3, after sorting (104), socks within each of the groups 6 may be identified with a group identifier 40 corresponding to the identifier 24 of the pouch 12 in which they are placed. For example, a patient having three socks with 1-ply, 3-ply, and 5-ply fabric thickness would be provided with a plurality 10 of pouches 12 with corresponding identifiers 24. The socks within each of the plurality 4 of groups 6 may be marked with a group identifier 40, and inserted into each pouch 12 with the corresponding identifier 24 in order to keep the socks 8 organized and easily identifiable.

The device for managing a plurality of groups of socks, adapted for use between a limb of a patient and a socket of a prosthetic, as described herein is expected to reduce the risk of losing or misplacing the socks, and to facilitate improved use and care of the socks.

The invention claimed is:

1. A device for managing a plurality of groups of socks, each said group comprising at least one sock, socks of each of said groups having different characteristics from one another, said device comprising:
    a plurality of pouches attached to one another, each said pouch adapted for containing at least one said sock from one of said groups, each said pouch comprising an identifier corresponding to one of said group, said identifiers comprise indicia selected from the group consisting of numbers, letters, Braille, and combinations thereof.

2. The device according to claim 1, wherein each of said plurality of pouches is attached to a substrate.

3. The device according to claim 1, wherein each said pouch defines an opening for receiving said socks.

4. The device according to claim 3, wherein at least one of said pouches further comprises a fastening device for closing said opening.

5. The device according to claim 4, wherein said fastening device is selected from a group consisting of: zippers, hook and loop fasteners, snap closures, buttons, and magnetic closures.

6. The device according to claim 4, wherein said fastening device is a zipper, said zipper comprising a zipper pull attached to said zipper, said zipper pull comprises an identifier corresponding to one of said group.

7. The device according to claim 1, wherein each said pouch is constructed of a washable material.

8. The device according to claim 1, wherein each said pouch is constructed of a quick-drying material.

9. The device according to claim 1, wherein each said pouch is constructed of a different colored material.

10. The device according to claim 9, wherein each said pouch is color coded, each said pouch corresponding to a respective one of said group of socks.

11. The device according to claim 1, wherein said patient education and compliance tool comprises instructions for use and care of said plurality of groups of socks.

12. The device according to claim 1, further comprising a fastener for removably attaching said patient education and compliance tool, thereto, said fastener selected from the group consisting of D-rings, hook and loop fasteners, and magnets.

13. The device according to claim 1, wherein at least one said pouch comprises a mesh material.

14. The device according to claim 1, wherein one said pouch is adapted for securing accessories.

15. The device according to claim 1, further comprising at least one patient education and compliance tool attached to said plurality of pouches.

16. A method for managing a plurality of groups of socks, each said group comprising at least one sock, socks of each of said groups having different characteristics from one another, said method comprising:
   sorting said plurality of groups of socks according to said characteristics of said socks;
   associating each said pouch with a respective one of said groups;
   securing each said group of socks within an associated one of said pouches respectively; and wherein
   said associating step comprises associating a unique identifier with each said pouch, said unique identifier being selected from the group consisting of numbers, letters, Braille, and combinations thereof.

17. The method according to claim 16, wherein sorting said plurality of groups of socks comprises sorting said socks according to a thickness of said socks.

18. The method according to claim 16, wherein sorting said plurality of groups of socks comprises associating a unique identifier with said socks within each said group of socks respectively.

* * * * *